United States Patent [19]
Jacobs

[11] B 3,981,176
[45] Sept. 21, 1976

[54] DUAL FREQUENCY ACOUSTIC GAS COMPOSITION ANALYZER

[75] Inventor: John E. Jacobs, Evanston, Ill.

[73] Assignee: The United States of America as represented by the Secretary of the Department of Health, Education and Welfare, Washington, D.C.

[22] Filed: Sept. 16, 1974

[21] Appl. No.: 506,744

[44] Published under the second Trial Voluntary Protest Program on January 13, 1976 as document No. B 506,744.

[52] U.S. Cl. .................................................... 73/24
[51] Int. Cl.² ......................................... G01N 29/02
[58] Field of Search ............... 73/24, 23, 67, 67.2, 73/69; 324/82 R, 83 R, 83 A

[56] References Cited
UNITED STATES PATENTS

| | | | |
|---|---|---|---|
| 3,429,177 | 2/1969 | Webb | 73/24 |
| 3,468,157 | 9/1969 | Burk et al. | 73/24 |
| 3,789,655 | 2/1974 | Passeri | 73/24 |

OTHER PUBLICATIONS

Stott, *Review of Scientific Instr.*, "Sonic Gas Analyzer for Measurement of $CO_2$ in Expired Air,", vol. 28 No. 11, pp. 914–915, Nov. 1957.
"National Bureau of Standards Tech. News Bulletin, "Propagation of Sound in Monatomic Gases," vol. 40, No. 9, Sept. 1956, pp. 121–124.

Staffin, *Control Engineering*, "6 Ways to Measure Phase Angle", Oct., 1965, pp. 78–83.

Primary Examiner—Richard C. Queisser
Assistant Examiner—Stephen A. Kreitman
Attorney, Agent, or Firm—Browdy and Neimark

[57] ABSTRACT

An apparatus for determining the composition of a gas by measuring the acoustic impedance and absorption of a gas at two distinct frequencies. The velocity variations due to the presence of a gas in a fixed length column are measured by comparing the phase of the voltage applied to a sending transducer to the phase of the voltage in a receiving transducer. Since the distance between the transducers is fixed, the phase variation is indicative of the velocity of the sound at any particular frequency. The output voltage obtained from a phase comparator is proportional to the phase difference and since the relationship between the concentration of the gas and the output voltage is known, the concentration of the gas is easily ascertained. The influence of temperature changes in the column are eliminated by summing the phase differences measured at the two distinct frequencies. In addition, by a judicious choice of frequencies, the amount of water vapor present in a particular gas may be compensated for.

4 Claims, 5 Drawing Figures

DUAL FREQUENCY ACOUSTIC GAS COMPOSITION ANALYZER

FIELD OF THE INVENTION

The present invention relates to an ultrasonic gas analyzer, and, more particularly, to an analyzer used in the monitoring of the respiratory function. The composition of the expired gas, particularly $CO_2$, is measured by the unique velocity dispersion of transmitted ultrasonic vibrations through a fixed length column.

BACKGROUND OF THE INVENTION

In a physiological study of the respiratory function a knowledge of the percentage of carbon dioxide in the expired air is quite helpful in determining the condition of the patient. The prior art shows several methods which have been used to accomplish this purpose. The first method employs an infra-red gas analyzer which consists of an infra-red source, a sample cell, a reference cell and a detector cell. The reference cell is divided into two compartments by a thin metal diaphragm which contains the same gas to be analyzed. Light passing through the sample cell differs in intensity from the light passing through the reference cell due to the absorption of the gas molecules in the sample cell. This results in a difference of pressure in the two compartments of the detector cell which moves the diaphragm and alters the capacitance between the diaphragm and the fixed plate in the detector cell.

A second method utilizes a mass spectrometer which accelerates and focuses gaseous ions (ionized by electrons emitted from a heated filament) by a combination of electric and magnetic fields. The traveling path or time-of-flight is determined by the pattern and strength of these fields and by the mass-to-charge ratio of the ions. Thus, ions of different molecular weight can be differentiated and their substance measured.

However, these two methods must utilize large, bulky and complicated devices to be effective. The present device, which utilizes the principle of sound velocity on the mean molecular weight of the component gas, promises a small-sized, more economic and less complicated device.

SUMMARY OF THE INVENTION

It is, accordingly, an object of the present invention to overcome the defects of the prior art, such as indicated above.

Another object is to provide for improved gas analysis.

Another object is to provide an ultrasonic gas analyzer which is small, economical, and easy to operate.

A further object is to provide an ultrasonic gas analyzer which compensates for the presence of water vapor in the gas to be measured.

Yet another object is to provide an ultrasonic gas analyzer for use in measuring the $CO_2$ composition of expired air.

When a sound wave passes through a gas, its velocity is determined by the density, pressure and temperature of the gas. A change in any of those variables will alter the velocity of the sound wave through that medium.

Stokes and Kichhoff discovered that sound waves are absorbed and dispersed in gasses as a result of their viscosity and thermal conduction. Experimentation has shown that this is true in monatomic gasses, such as argon and xenon. If we assume that viscosity and heat conduction act independently in producing an absorption of sound waves, then the coefficient of absorption can be expressed by $$\alpha = \frac{\omega^2}{2\rho_0 V_0^3} \left[ \frac{4\eta}{3} - \frac{K(\gamma-1)}{C_p} \right]$$

with $$\gamma = 1 + \frac{R}{C_v} \qquad (1)$$

where
$K$ = the thermal conductivity of the gas
$\eta$ = coefficient of shear viscosity
$C_p$ = heat capacity at constant pressure
$V_0$ = velocity of propagation
$\rho_0$ = density of the gas at rest
$R$ = the gas constant
$C_v$ = heat capacity at constant volume
$\omega$ = frequency However, for polyatomic gasses, such as $O_2$, $N_2$, $H_2O$ and $CO_2$, Herzfeld and Rice determined that the sound absorption and dispersion are primarily due to thermal relaxation. This relaxation effect is a result of an additional loss mechanism inherent in molecular gasses. As a sound wave progresses in a molecular gas, part of the compressional energy is stored in the vibrational and rotational degrees of freedom of the molecules. Since this storage involves excitation and de-excitation of internal energy states during collision, it requires time, and a phase lag between the internal and translational modes of the gas results.

Since the velocity of propagation may be expressed as $$V_o^2 = \frac{C_p}{C_v} \frac{RT}{M} \qquad (2)$$

where
M = gram molecular weight of the gas
T = temperature

The relaxation effect can be taken into account by introducing the frequency-dependent and complex heat capacities $C_p^{dyn}$ and $C_v^{dyn}$ into Equation 2.

If the transport processes are neglected and only the internal mode for the energy with a single relaxation time $\tau$ is considered, then $$C_p^{dyn} = C_p^\infty + \frac{C'}{1 + \gamma \omega \tau} \qquad (3)$$

where $C_p^\infty$ is the high frequency limit of specific heat at constant pressure and $C'$ is the internal specific heat. For calculation purposes, $\tau$ can be determined from the reaction rate if the scheme of the reaction is known, and $C'$ can be determined from the Plank-Einstein formula. Then the well known S-shaped dispersion curve for the velocity can be calculated from $$V^2 = \frac{P}{\rho} Re \frac{C_p^{dyn}}{C_v^{dyn}} \qquad (4)$$

Where P = pressure of the gas

In the case of polyatomic gasses or mixtures of gasses, there is more than one storage mode for the internal energy that must be considered. Those modes are the rotational and vibrational degrees of freedom. Research has shown that the frequency range for absorption is well below the rotational relaxational frequency and the contributions owing to rotation give a term which is linear in frequency for frequencies less than 1 MHz. There is also negligible velocity dispersion in this range as a result of the rotation. When these assumptions are made, the absorption due to relaxation effects is $$\alpha_{relaxation} = \alpha_{rotation} - \alpha_{vibration} \qquad (5)$$

For the vibrational relaxational processes, a simple extension of the addition technique would lead to $$C_{vib}^{dyn} = \Sigma \frac{C_i'}{1 + \gamma \omega \tau_i} \qquad (6)$$

as a representation of the vibrational dynamic heat capacity where $C_i'$ refers to the vibrational heat capacity and the $\tau$'s are closely connected to the lifetimes of the corresponding vibrational quantas.

Thus, as can be noted from the above equations, the velocity of the sound wave varies according to the mass molecular weight of the gas and also its density. It was just this phenomenon which is utilized in the present invention.

According to the present invention, two signals are generated and then passed to a brass column containing the gas to be analyzed. The phase difference due to the passage of each of the sound waves through the gas is measured and expressed in terms of an electrical voltage. These voltages are then compared and the difference in voltage is used to determine the concentration of the particular gas in the column.

It should be noted that the present gas analyzer contains two and not one variable frequency oscillator. The difficulty with a single channel velocity dispersion measurement system is that the velocity dispersion of the ultrasonic waves is dependent upon the amount of water vapor contained within the gas. The frequency of maximum velocity dispersion, which is unique to a specific gas, depends to some extent upon the temperature as well as the amount of water vapor present in the gas. In the present device, the frequency of 25 kHz is selected because that is the frequency at which carbon dioxide exhibits the maximum dispersion and thus this is the frequency at which the sensitivity to $CO_2$ is the greatest. The frequency of 40 kHz was selected since that is the frequency at which the velocity of dispersion of the carbon dioxide due to the added moisture and temperature variations is essentially that of the 25 kHz signal.

In the instrument as presently disclosed, the phase difference of the two frequencies is independently measured and expressed in terms of voltage. This voltage indirectly measures the velocity variation in the medium by comparing the phase of the voltage applied to the sending transducer to that obtained at the receiving transducer. Since the distance the sound wave travels is fixed, the phase variation is indicative of the velocity of the sound at that particular frequency.

A final output voltage is obtained by summing the signal obtained using the 40 kHz frequency with that of the 25 kHz frequency. Since the device was previously calibrated to indicate the relationship between the final output voltage and the concentration of $CO_2$ present in expired gas, the particular concentration of the $CO_2$ can easily be determined and the water vapor present compensated for.

It should be noted that while this particular device has been described for measuring the $CO_2$ composition of a specific gas, the composition of any gas in the expired air may similarly be measured once the proper frequencies of the generators are determined.

For a better understanding of the invention, a possible embodiment thereof will be described with reference to the attached drawing, it being understood that this embodiment is exemplary and not limitative.

DESCRIPTION OF THE PREFERRED EMBODIMENT

Figure 2:
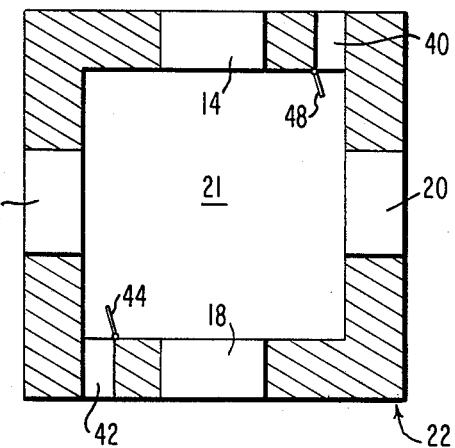
FIG. 2 is a cross section of the acoustical column of the analyzer.

Referring now to the drawing, FIG. 2 shows a cross section of a fixed length column 22 into which the gas to be measured is introduced. The column is provided with a gas inlet valve 42 which will allow the testing sample gasses to be pumped or blown into the inner reservoir 21 of the tube and a gas outlet conduit 40 which allows the tested gas to be extracted from the column. Both these conduits 40 and 42, may be opened and closed by any conventional means such as dampers 44 and 48. The column 22 can be constituted of any suitable material such as brass or any other material inert to the gas.

Figure 1:
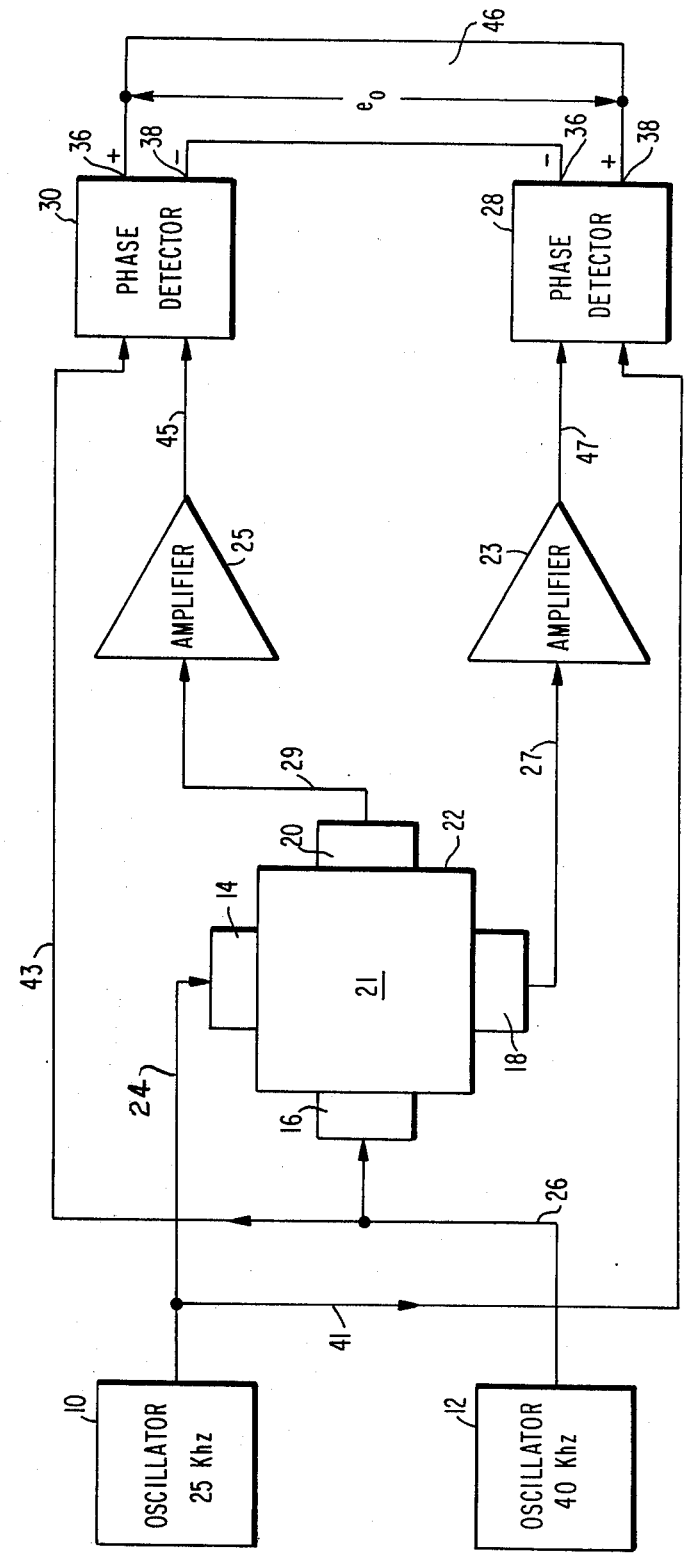
FIG. 1 shows a schematic drawing of the acoustic gas analyzer.

Once the gas is introduced into the column the two variable frequency oscillators 10 and 12, (FIG. 1) should be set to the required operational frequencies for minimizing the effect of the water vapor on the particular gas to be tested. In the case of the present instrument, the frequency of 25 kHz was selected as being the one which carbon dioxide exhibits its maximum velocity dispersion, while the frequency of 40 kHz was selected as being the frequency at which the velocity dispersion of the carbon dioxide due to the added moisture and temperature variations is essentially that of the 25 kHz signal. Since the final output signal is obtained by summing the signal obtained from the 40 kHz with that received using the 25 kHz frequency, the carbon dioxide sensitivity obtained at 25 kHz is obtained and the variation due to humidity and temperature variations is compensated by the 40 kHz channel.

When the device is activated, each signal generator 10 and 12 supplies square waves of 5 volts through electrical connectors 24 and 26, to each conventional transmitting crystal or transducer 14 and 16 mounted on the outer surface of the column 22. These square waves are simultaneously supplied to each respective phase detector 28 and 30 by way of electrical connections 41 and 43, in order to measure the phase difference. The transmitting crystals 14 and 16 convert the electrical energy to mechanical energy and generate a sound wave. The sound wave passes through the tube in the direction perpendicular to the axis of the tube and reaches the conventional receiving crystals or transducers 18 and 20 mounted on the opposite outer surface of the tube 22 facing each respective transmitting crystal 14 and 16. These receiving crystals 18 and 20 convert the received mechanical energy back to electrical energy. The electrical signal is fed through electrical lines 27 and 29 into amplifiers 23 and 25 which produces an output voltage. Standard amplifiers such as RCA 3035 may be employed to amplify the electrical energy.

The output signal from the amplifiers and the original signal from the generators will have a phase difference due to the finite transit time in the tube. The phase difference $\phi$ can be expressed as the equation:

$$\phi = \frac{2\pi d}{\lambda}$$

where $d$ is the distance between the transmitting crystal and the receiving crystal and $\lambda$ is the wave length. The velocity can now be obtained by means of the following equation:

$$V = \frac{2(d \cdot f)}{\phi}$$

where $f$ is the frequency.

The amplified electrical energy is then passed on to the phase detectors 28 and 30 of electrical lines 45 and 47. The phase difference is measured by conventional phase detectors 28 and 30 such as RCA 3082 and thus the output voltage of each phase detector obtained from pins 36 and 38 is proportional to the phase difference.

The final output voltage $e_o$ is obtained by summing the measured dispersion at 40 kHz with that at 25 kHz. This output voltage may be read from any conventional output means 46, such as oscilloscope. Since these phase detectors are operated in the saturation range, any variation due to the absorption by the medium will not affect the output voltage phase difference relationship; and thus the variation of voltage due to the absorption by the medium can be neglected.

Since the main purpose of this device is to determine the composition, mainly the $CO_2$ concentration, of a sample gas under investigation, an explicit relation between concentration and the measured voltage thus must be established. Because the concentration difference results in the velocity difference and then the phase shift, it is necessary to determine the characteristics of each particular phase detector. The sensitivity of each machine will vary, however, they will all be in approximately the same range. After investigation, the device described herein exhibited a sensitivity of 0.04 volts for every degree of phase shift in its linear operation range.

Figure 3:
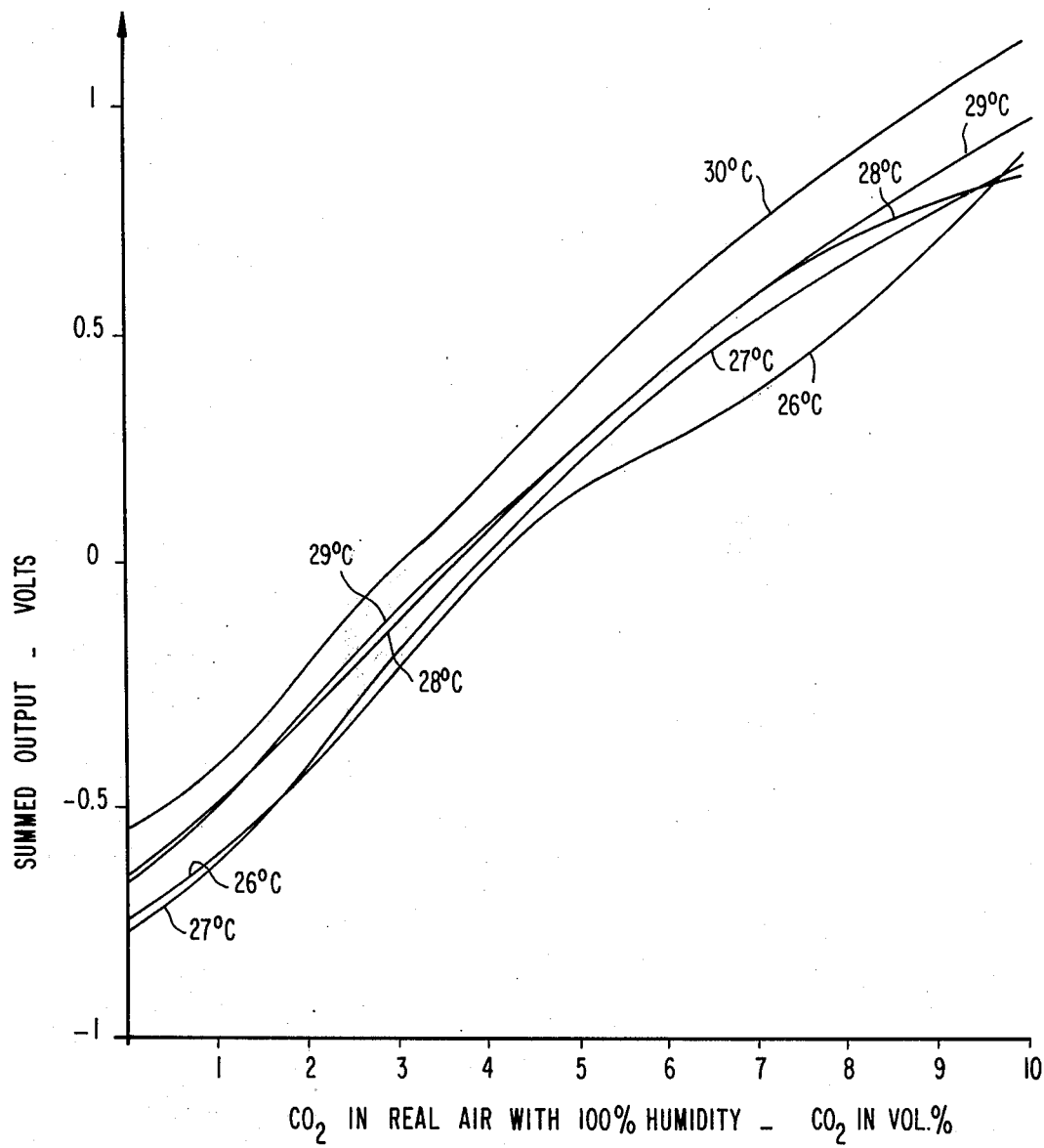
FIGS. 3, 4, 5 are graphical representations of the output voltage and the percentage of $CO_2$ at different temperatures.
Figure 4:
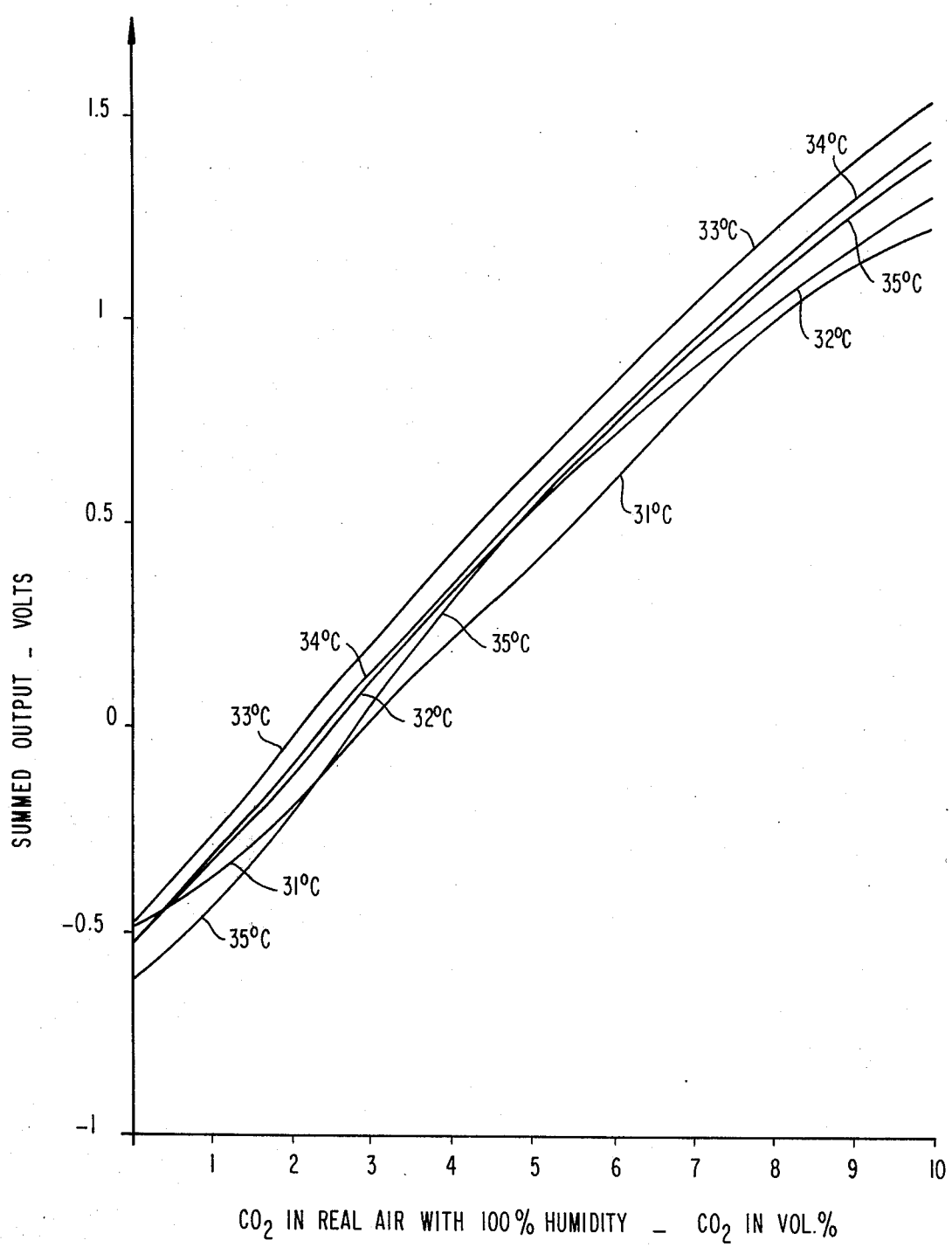
Figure 5:
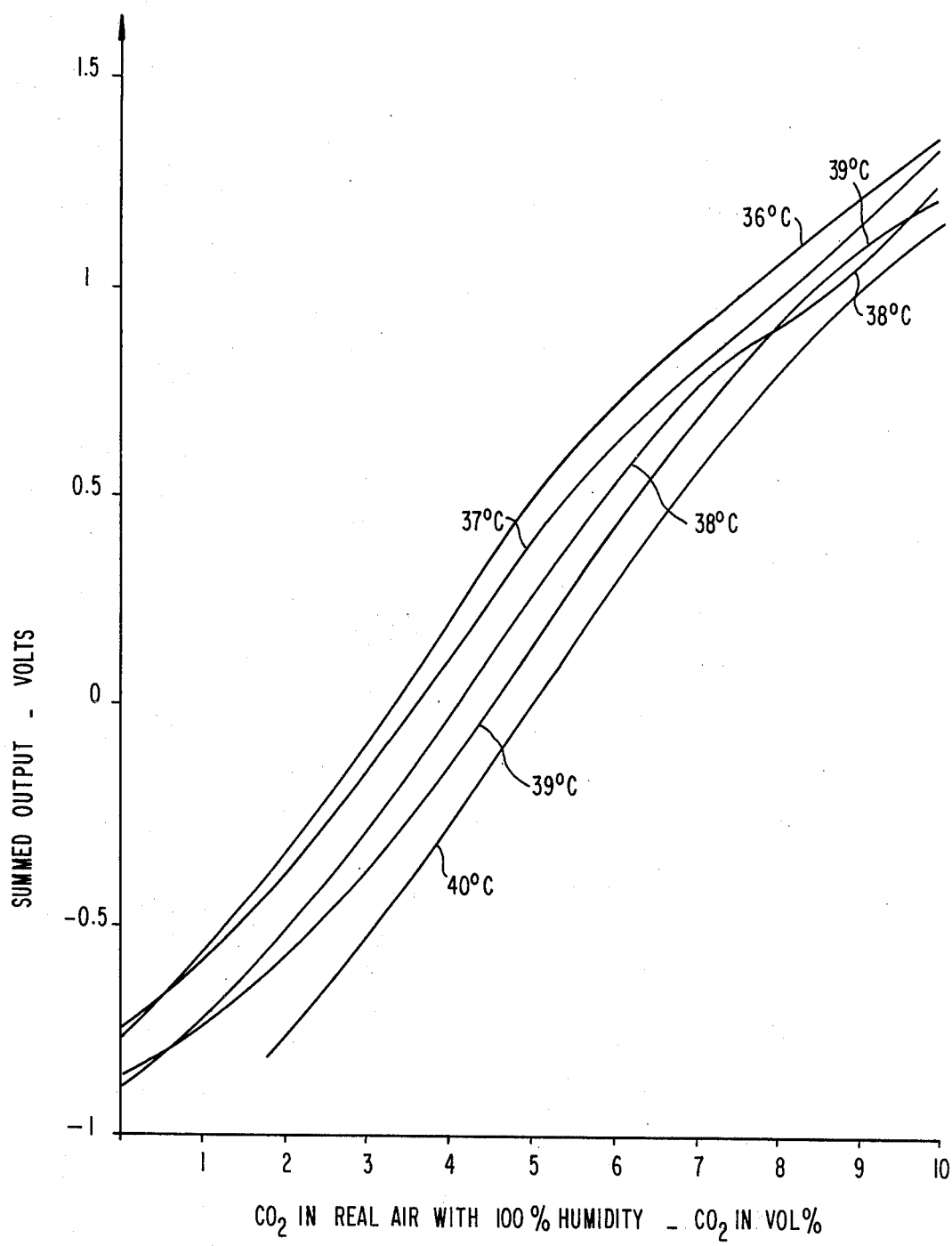

Due to the fact that the velocity dispersion is affected by the temperature and the margin of error of each instrument is different, the relationship of the voltage output to the concentration of the $CO_2$ must be determined for each device. Typical graphical representations are shown in FIGS. 3, 4 and 5. Since the normal expired air from humans contains about 5 percent of $CO_2$, samples ranging from 0 to 10 percent of the $CO_2$ in the air were investigated. 100 percent humidified samples were used since the expired gas from humans is always 100 percent humidified. It must be noted that the values are expressed in the voltage concentration relationship without referring to the corresponding velocities. This device is installed in an environment which has a room temperature of about 25°C. while the expired air has the temperature of 37°C or higher; so it is necessary to investigate the behavior during the course of the change of temperatures from 25° to 40°C.

The ability of this device to measure sound velocities in several media was confirmed by introducing air, oxygen, nitrogen and carbon dioxide into it. The values obtained are shown in Table I and are corrected to 25°C by the classical temperature correction.

$$V_{25\ ^{\circ}C} = V_{t\ ^{\circ}C} [(273 + 25)(273 + t)]^{1/2}$$

for comparison with the values obtained by other methods, where t equals the temperature of the medium measured.

From this data it may be seen that this device is capable of measuring sound velocities.

TABLE I

| | Velocity of sound at 25°C | | | |
|---|---|---|---|---|
| | freq. = 25KHz | | freq. = 40KHz | |
| gasses | $V_1$(m/sec) | $V_2$(m/sec) | $V_1$(m/sec) | $V_2$(m/sec) |
| Air | 346.6 | 342.4 | 346.6 | 341.6 |
| $O_2$ | 328.9 | 326.5 | 328.9 | 327.8 |
| $N_2$ | 354.0 | 349.8 | 354.0 | 353.8 |
| $CO_2$ | 273.6 | 269.1 | 276.2 | 278.5 |

Note:
$V_1$: Values obtained by other methods
$V_2$: Values obtained by the present experiment It will be obvious to those skilled in the art that various changes may be made without departure from the scope of the invention and the invention is not to be considered limited to what is shown in the drawings and described in the specification.

What is claimed is:

1. An apparatus for measuring the composition of a gas comprising:
    a fixed length acoustical column containing the gas to be tested;
    first and second variable frequency oscillator means for simultaneously generating respectively first and second different oscillating signals;
    first and second transmitting transducer means, disposed on said column, for converting said first and second oscillating signals into mechanical energy;
    first and second receiving transducer means disposed on said column for converting the mechanical energy produced by said transmitting transducer means into first and second electrical energy output signals, wherein said first transmitting transducer means is disposed on said acoustical column opposite said first receiving means, and said second transmitting transducer means is disposed on said acoustical column opposite said second receiving transducer means, and wherein said first and second transmitting means and said first and second receiving transducer means are disposed on said acoustical column in order to pass both acoustic beams across the same gap;
    first phase detector means, connected to said first transmitting transducer and said first receiving transducer means, for measuring the phase shift in said first oscillating signal and generating a first phase shift output signal;
    second phase detector means, connected to said second transmitting transducer and said second receiving transducer, for measuring the phase shift in said second oscillating signal and generating a second phase shift output signal; and output means, connected to said first and second phase detector means, for summing said first and second phase shifts output signals.

2. An apparatus for measuring the composition of a gas according to claim 1 wherein when the gas in said acoustical column is $CO_2$, the frequencies of said first and second oscillating signals of said first and second variable frequency oscillator means are, respectively, 25 kHz and 40 kHz.

3. An apparatus for measuring the composition of a gas, according to claim 1 further comprising first and second amplifying means, connected respectively between said first receiving transducer means and said first detector means, and said second receiving transducer means and said second detector means for amplifying said first and second electrical energy output signals produced by said first and second receiving transducer means.

4. An apparatus for measuring the composition of a gas according to claim 1 wherein said fixed length acoustical column contains a means for introducing the gas into the column; and, a means for extracting the gas from the column.

* * * * *